United States Patent
Wong et al.

(10) Patent No.: US 6,726,918 B1
(45) Date of Patent: Apr. 27, 2004

(54) METHODS FOR TREATING INFLAMMATION-MEDIATED CONDITIONS OF THE EYE

(75) Inventors: Vernon G. Wong, Menlo Park, CA (US); Mae W. L. Hu, Los Altos Hills, CA (US)

(73) Assignee: Oculex Pharmaceuticals, Inc., Sunnyvale, CA (US)

( * ) Notice: Subject to any disclaimer, the term of this patent is extended or adjusted under 35 U.S.C. 154(b) by 0 days.

(21) Appl. No.: 09/693,008

(22) Filed: Oct. 20, 2000

Related U.S. Application Data

(60) Provisional application No. 60/216,236, filed on Jul. 5, 2000.

(51) Int. Cl.⁷ .................................................. A61F 13/00
(52) U.S. Cl. ........................ 424/422; 424/400; 424/423; 424/426; 424/427; 424/428; 424/429
(58) Field of Search ................................. 424/400, 422, 424/423, 426, 427, 428, 489

(56) References Cited

U.S. PATENT DOCUMENTS

| | | | | |
|---|---|---|---|---|
| 3,914,402 A | * | 10/1975 | Shell ............................ | 424/32 |
| 3,986,510 A | * | 10/1976 | Higuchi et al. ............. | 128/260 |
| 4,180,646 A | * | 12/1979 | Choi et al. ................... | 528/153 |
| 4,863,457 A | * | 9/1989 | Lee .......................... | 604/891.1 |
| 5,378,475 A | | 1/1995 | Smith et al. | |
| 5,773,019 A | | 6/1998 | Ashton et al. | |
| 5,902,598 A | | 5/1999 | Chen et al. | |
| 6,046,187 A | * | 4/2000 | Berde et al. ................ | 514/180 |
| 6,063,116 A | * | 5/2000 | Kelleher ........................ | 623/4 |
| 6,074,661 A | * | 6/2000 | Olejnik et al. .............. | 424/427 |

OTHER PUBLICATIONS

Aguilar, H. E. et al., (1995). "Vancomycin Levels After Intravitreal Injection,"*Retina*15:428–432.
Araie, M. and Maurice, D. M. (1991). "The Loss of Fluorescein, Fluorescein Glucuronide and Fluorescein Isothiocyanate Dextran From the Vitreous by the Anterior and Retinal Pathways,"*Exp. Eye. Res.*52;27–39.
Barza, M. et al., (1983). "Pharmacokinetics of Intravitreal Carbenicillin, Cefazolin, and Gentamicin in Rhesus Monkey,"*Invest. Ophthalmol. Vis. Sci.*24:1602–1606.
Ben–Nun, J. et al., (1989). "Pharmacokinetics of Intravitreal Injection,"*Investigative Ophthalmology & Visual Science*30(6):1055–1061.
Challa, J. K. et al., (1998). "Exudative Macular Degeneration and Intravitreal Triamcinolone: 18month follow up,"*Australian and New Zealand Journal of Ophthalmology*26:277–281.
Enyedi, L. B. et al., (1996) "An Intravitreal Device Providing Sustained Release of Cyclosporine and Dexamethasone," *Current Eye Research,*pp. 549–557.
Fatt, R. (1975) "Flow and Diffusion In The Vitreous Body of The Eye,"*Bulletin of Pharmaceutical Biology*37:85–90.

Friedrich, S. et al. (1997). "Finite Element Modeling of Drug Distribution in the Vitreous Humor of the Rabbit Eye,"*Annals of Biomedical Engineering*25:303–314.
Hainsworth, D.P. (1996). "Sustained Release Intravitreal Dexamethasone,"*Journal of Ocular Pharmacology and Therapeutics*12(1):57–63.
Hayreh, S.S. (1996). "Posterior Drainage of the Intracular Fluid From the Vitreous,"*Exp. Eye. Res.*5:123–144.
Jaffe, G. J. et al., (1999). "Safety, Efficacy, and Pharmacokinetics of an Intravitreal Fluocinolone Sustained Drug Delivered System,"*Investigative Ophthalmology & Visual Science*40(4):5988, Abstract no. 5195.
Jay, W. M. et al., (1987). "Intravitreal Ceftazidine in a Rabbit Model: Dose–and Time–Dependent Toxicity And Pharmacokinetic Analysis,"*J. Ocular Pharmacology*3(3):257–262.
Johnson, F. and Maurice, D. (1984). "A Simple Method of Measuring Aqueous Humor Flow With Intravitreal Fluoresceinated Dextrans,"*Exp. Eye. Res.*39:791–805.
Kane, A. et al., (1981). "Intravitreal Injection of Gentamicin in Rabbits,"*Invest. Ophthalmol. Vis. Sci.*20(5):593–597.
Kimura, H. and Ogura, Y. (2001). "Biodegradable Polymers for Ocular Drug Delivery,"*Ophthalmologica*215:143–155.
Kralinger, M. T. et al., (2001). "Slow Release of Acetylsalicylic Acid by Intravitreal Silicone Oil,"*Retina, The Journal of Retinal and Vitreous Diseases,*21(5):513–520.
Laurent, U. B. G. and Fraser, J. R. E. (1983). "Turnover of Hyaluronate in the Aqueous Humour And Vitreous Body of the Rabbit,"*Exp. Eye. Res.*36:493–504.
Maurice, D. M. and Mishima, S. (1984). "Chapter 2: Ocular Pharmacokinetics,"*Handbook of Experimental Pharmacology,*vol. 69, M. L. Sears (eds.), Springer–Verlag, pp. 19–116.
Maurice, D. M. (1957). "The Exchange of Sodium Between The Vitreous Body and The Blood And Aqueous Humor,"*J. Physiol.*137:110–125.
Maurice, D. M. (1987). "Flow of Water Between Aqueous and Vitreous Compartments in the Rabbit Eye,"*Am. J. Physiol.*252(Renal Fluid Electrolyte Physiol. 21):F104–F108.
Moseley H. et al., (1984). "Routes of Clearance of Radioactive Water From The Rabbit Vitreous,"*British Journal of Ophthalmology*68:145–151.

(List continued on next page.)

Primary Examiner—Thurman K. Page
Assistant Examiner—Charesse Evans
(74) Attorney, Agent, or Firm—Morrison & Foerster LLP

(57) ABSTRACT

Methods for treating inflammation-mediated conditions of the eye are described, comprising: implanting into the vitreous of the eye of an individual a bioerodible implant comprising a steroidal anti-inflammatory agent and a bioerodible polymer, wherein the implant delivers the agent to the vitreous in an amount sufficient to reach a concentration equivalent to at least about 0.05 μg/ml dexamethasone within about 48 hours and maintains a concentration equivalent to at least about 0.03 μg/ml dexamethasone for at least about three weeks.

42 Claims, No Drawings

OTHER PUBLICATIONS

Ohtori, A. and Tojo, K. (1994). "*In vivo/ in Vitro* Correlation of Intravitreal Delivery of Drugs With the Help of Computer Simulation,"*Biol. Pharm, Bull.*17(2):283–290.

Pearson, P. A. et al, (1993) "Clearance and Distribution of Ciprofloxacin After Intravitreal Injection," *Retina*13:326–330.

Rootman, D. S. et al., (1992). "Toxicity and Pharmacokinetics of Intravitreally Injection Ciprofloxacin in Rabbit Eyes,"*Can. J. Ophthalmol.*27(6):277–282.

Sasaki, H. et al., (1999). "Drug Absorption Behavior After Periocular Injections,"*Biol. Pharm. Bull.*22(9):956–960.

Schindler, R. H. et al., (1982) "The Clearance of Intravitreal Triamcinolone Acetonide,"*American Journal of Ophthalmology*93:415–417.

Scholes, G. N. et al., (1985). "Clearance of Triamcinolone From Vitreous,"*Arch. Ophthalmol.*103:1567–1569.

Xu, J. et al., (2000). "Permeability and Diffusion in Vitreous Humor: Implications for Drug Delivery,"*Pharmaceutical Research*17(6):664–667.

* cited by examiner

METHODS FOR TREATING INFLAMMATION-MEDIATED CONDITIONS OF THE EYE

CROSS-REFERENCE TO OTHER APPLICATIONS

This application claims priority to U.S. Provisional Application Ser. No. 60/216,236, filed Jul. 5, 2000, entitled "Dexamethasone Posterior Segment Drug Delivery System for Treatment of Severe Uveitis", the disclosure of which is incorporated herein by reference.

TECHNICAL FIELD

This invention relates to methods for treating inflammation-mediated conditions of the eye by implanting into the vitreous of the eye a bioerodible implant comprising a steroidal anti-inflammatory agent and a bioerodible polymer. Specifically, these methods may be used in the protection and treatment of tissues damaged by or susceptible to damage by inflammation-mediated conditions such as uveitis, by providing therapeutic levels of an anti-inflammatory agent to the vitreous of the eye.

BACKGROUND ART

Glucocorticoids are an important part of treatment in severe anterior, intermediate, posterior, and panuveitis. A major problem with present drug therapy is the inability to achieve adequate intraocular drug concentration. In particular, uveitis is well known for its long duration due in part to the difficulties associated with poor intraocular penetration of topical medications into the posterior segment (Bloch-Michel E. (1992). "Opening address: intermediate uveitis," In *Intermediate Uveitis, Dev Ophthalmol.* W. R. F. Böke et al. eds., Basel: Karger, 23:1–2; Pinar, V. *Intermediate uveitis*. Massachusetts Eye & Ear Infirmary Immunology Service at <http://www.immunology.meei.harvard.edu/imed.htm> (visited in 1998); Rao, N. A. et al. (1997). "Intraocular inflammation and uveitis" In *Basic and Clinical Science Course.* Section 9 (1997–1998) San Francisco: American Academy of Ophthalmology, pp. 57–80, 102–103, 152–156; Böke, W. (1992). "Clinical picture of intermediate uveitis," In *Intermediate Uveitis, Dev Ophthalmol.* W. R. F. Böke et al. eds., Basel: Karger, 23:20–7; Cheng C-K et al. (1995). "Intravitreal sustained-release dexamethasone device in the treatment of experimental uveitis," *Invest Ophthalmol Vis Sci.* 36:442–53). Systemic glucocorticoid administration may require prolonged exposure of high plasma concentrations (administration of 1 mg/kg/day for 2–3 weeks) so that therapeutic levels can be achieved in the eye (Pinar, V. "Intermediate uveitis," Massachusetts Eye & Ear Infirmary Immunology Service at <http://www.immunology.meei.harvard.edu/imed.htm> (visited in 1998)). These high drug plasma levels often lead to systemic side effects such as hypertension, hyperglycemia, increased susceptibility to infection, peptic ulcers, psychosis, and other complications (Cheng C-K et al. (1995). "Intravitreal sustained-release dexamethasone device in the treatment of experimental uveitis," *Invest Ophthalmol Vis Sci.* 36:442–53; Schwartz, B. (1966). "The response of ocular pressure to corticosteroids," *Ophthalmol Clin North Am* 6:929–89; Skalka, H. W. et al. (1980). "Effect of corticosteroids on cataract formation," Arch Ophthalmol 98:1773–7; Renfro, L. et al. (1992). "Ocular effects of topical and systemic steroids," *Dermatologic Clinics* 10:505–12). In addition, overall drug delivery to the eye may be poor due to the short drug plasma half-life limiting exposure into intraocular tissues. The most efficient way of delivering drug to the posterior segment is to place it directly in the vitreous (Maurice, D. M. (1983). "Micropharmaceutics of the eye," *Ocular Inflammation Ther* 1:97–102; Lee, V. H. L. et al. (1989). "Drug delivery to the posterior segment" Chapter 25 In *Retina.* T. E. Ogden and A. P. Schachat eds., St. Louis: C V Mosby, Vol. 1, pp.483–98; Olsen, T. W. et al. (1995). "Human scleral permeability: effects of age, cryotherapy, transscleral diode laser, and surgical thinning," *Invest Ophthalmol Vis Sci* 36:1893–1903). Intravitreal injections have shown promising results, however, due to the short intraocular half-life of glucocorticoids (approximately 3 hours), intravitreal injections must be repeated to maintain drug levels which increases the potential for side effects such as retinal detachment, endophthalmitis, and cataract (Maurice, D. M. (1983). "Micropharmaceutics of the eye," *Ocular Inflammation Ther* 1:97–102; Olsen, T. W. et al. (1995). "Human scleral permeability: effects of age, cryotherapy, transscleral diode laser, and surgical thinning," *Invest Ophthalmol Vis Sci* 36:1893–1903; Kwak, H. W. and D'Amico, D. J. (1992). "Evaluation of the retinal toxicity and pharmacokinetics of dexamethasone after intravitreal injection," *Arch Ophthalmol* 110:259–66). Topical, systemic, and periocular glucocorticoid treatment must be monitored closely due to toxicity and the long-term side effects associated with chronic systemic drug exposure sequelae (Rao, N. A. et al. (1997). "Intraocular inflammation and uveitis" In *Basic and Clinical Science Course.* Section 9 (1997–1998) San Francisco: American Academy of Ophthalmology, pp. 57–80, 102–103, 152–156; Schwartz, B. (1966). "The response of ocular pressure to corticosteroids," *Ophthalmol Clin North Am* 6:929–89; Skalka, H. W. and Pichal, J. T. (1980). "Effect of corticosteroids on cataract formation," *Arch Ophthalmol* 98:1773–7; Renfro, L and Snow, J. S. (1992). "Ocular effects of topical and systemic steroids," *Dermatologic Clinics* 10:505–12; Bodor, N. et al. (1992). "A comparison of intraocular pressure elevating activity of loteprednol etabonate and dexamethasone in rabbits," *Current Eye Research* 11:525–30). U.S. Pat. No. 5,501,856 discloses controlled-release pharmaceutical preparations for intraocular implants to be applied to the interior of the eye after a surgical operation for disorders in retina/vitreous body or for glaucoma.

U.S. Pat. No. 5,869,079 discloses combinations of hydrophilic and hydrophobic entities in a biodegradable sustained release implant, and describes a polylactic acid polyglycolic acid (PLGA) copolymer implant comprising dexamethasone. As shown by in vitro testing of the drug release kinetics, the 100–120 µg 50/50 PLGA/dexamethasone implant disclosed did not show appreciable drug release until the beginning of the fourth week.

U.S. Pat. No. 5,824,072 discloses implants for introduction into a suprachoroidal space or an avascular region of the eye, and describes a methylcellulose implant comprising dexamethasone.

U.S. Pat. Nos. 4,997,652 and 5,164,188 disclose biodegradable ocular implants comprising microencapsulated drugs, and describes implanting microcapsules comprising hydrocortisone succinate into the posterior segment of the eye.

U.S. Pat. No. 5,164,188 discloses encapsulated agents for introduction into the suprachoroid of the eye, and describes placing microcapsules and plaques comprising hydrocortisone into the pars plana.

U.S. Pat. Nos. 5,443,505 and 5,766,242 discloses implants comprising active agents for introduction into a suprachoroidal space or an avascular region of the eye, and describes placing microcapsules and plaques comprising hydrocortisone into the pars plana.

Zhou et al. disclose a multiple-drug implant comprising 5-fluorouridine, triamcinolone, and human recombinant tissue plasminogen activator for intraocular management of proliferative vitreoretinopathy (PVR) (Zhou, T, et al. (1998). "Development of a multiple-drug delivery implant for intraocular management of proliferative vitreoretinopathy," *Journal of Controlled Release* 55: 281–295.)

There is a continued need for efficacious intraocular sustained release drug therapies for patients with inflammatory conditions.

All references cited herein are hereby incorporated by reference in their entirety.

DISCLOSURE OF THE INVENTION

The present invention provides a method for treating an inflammation-mediated condition of the eye, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.05 µg/ml dexamethasone within about 48 hours and maintains a concentration equivalent to at least about 0.03 µg/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.05 µg/ml dexamethasone within about 48 hours, and maintains a concentration equivalent to at least about 0.03 µg/ml dexamethasone for at least about three weeks.

In another embodiment of the invention, a method for treating an inflammation-mediated condition of the eye is provided, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.2 µg/ml dexamethasone within about 6 hours and maintains a concentration equivalent to at least about 0.01 µg/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.2 µg/ml dexamethasone within about 6 hours, and maintains a concentration equivalent to at least about 0.01 µg/ml dexamethasone for at least about three weeks.

MODES FOR CARRYING OUT THE INVENTION

Definitions

As used herein, the term "inflammation-mediated condition of the eye" is meant to include any condition of the eye which may benefit from treatment with an anti-inflammatory agent, and is meant to include, but is not limited to, uveitis, macular edema, acute macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion.

The term "bioerodible polymer" refers to polymers which degrade in vivo, and wherein erosion of the polymer over time is required to achieve the agent release kinetics according to the invention. Specifically, hydrogels such as methylcellulose which act to release drug through polymer swelling are specifically excluded from the term "bioerodible polymer". The terms "bioerodible" and "biodegradable" are equivalent and are used interchangeably herein.

The terms "steroidal anti-inflammatory agent" and "glucocorticoid" are used interchangeably herein, and are meant to include steroidal agents, compounds or drugs which reduce inflammation when administered at a therapeutically effective level.

"A concentration equivalent to dexamethasone", as used herein, refers to the concentration of a steroidal anti-inflammatory agent necessary to have approximately the same efficacy in vivo as a particular dose of dexamethasone. For example, hydrocortisone is approximately twentyfive-fold less potent than dexamethasone, and thus a 25 mg dose of hydrocortisone would be equivalent to a 1 mg dose of dexamethasone. One of ordinary skill in the art would be able to determine the concentration equivalent to dexamethasone for a particular steroidal anti-inflammatory agent from one of several standard tests known in the art. Relative potencies of selected corticosteroids may be found, for example, in Gilman, A. G., et al., eds. (1990). *Goodman and Gilman's: The Pharmacological Basis of Therapeutics*. 8th Edition, Pergamon Press: New York, p.1447.

An "individual" is a vertebrate, preferably mammal, more preferably a human. Mammals include, but are not limited to, humans, sport animals and pets, such as dogs, horses.

The terms "injury" or "damage" as used herein are interchangeable and refer to the cellular and morphological manifestations and symptoms resulting from an inflammatory-mediated condition, such as, for example, inflammation.

The term "treating" as used herein, means to reduce or prevent ocular injury or damage.

The term "therapeutic levels" as used herein, refers to the level of agent needed to reduce or prevent ocular injury or damage.

By "measured under infinite sink conditions in vitro," is meant assays to measure drug release in vitro, wherein the experiment is designed such that the drug concentration in the receptor medium never exceeds 5% of saturation. Examples of suitable assays may be found, for example, in (USP 23; NF 18 (1995) pp. 1790–1798). "A", "an" and "the" include plural references unless the context clearly dictates otherwise.

Methods for Treating an Inflammation-Mediated Condition

Intraocular glucocorticoid drug delivery systems made of a biodegradable polymer matrix have been developed which can release drug loads over various programmed time periods. These drug delivery systems which when inserted into the vitreous provide therapeutic levels of glucocorticoid for extended periods of time (e.g., 3 weeks or more). In particular, these delivery systems provide an initial "loading dose" level of drug of at least about 0.05 µg/ml dexamethasone equivalent to the posterior segment of the eye. These delivery systems have shown unexpected results in treating diseases such as uveitis and PVR.

Accordingly, the present invention provides a method for treating an inflammation-mediated condition of the eye, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.05 $\mu$g/ml dexamethasone within about 48 hours and maintains a concentration equivalent to at least about 0.03 $\mu$g/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.05 $\mu$g/ml dexamethasone within about 48 hours, and maintains a concentration equivalent to at least about 0.03 $\mu$g/ml dexamethasone for at least about three weeks.

In another embodiment of the invention, a method for treating an inflammation-mediated condition of the eye is provided, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.2 $\mu$g/ml dexamethasone within about 6 hours and maintains a concentration equivalent to at least about 0.01 $\mu$g/ml dexamethasone for at least about three weeks.

In another embodiment of the invention, a method for treating an inflammation-mediated condition of the eye is provided, comprising: implanting a solid body into the vitreous of the eye, said body comprising particles of a steroidal anti-inflammatory agent entrapped within a bioerodible polymer, whereby said agent is released from the body by erosion of the polymer, and whereby said agent is delivered to the vitreous at a rate and for a time sufficient to reach a concentration equivalent to at least about 0.2 $\mu$g/ml dexamethasone within about 6 hours, and maintains a concentration equivalent to at least about 0.01 g/ml dexamethasone for at least about three weeks.

Preferred inflammation-mediated conditions of the eye which may be treated by the methods of the invention include uveitis, macular edema, acute macular degeneration, retinal detachment, ocular tumors, fungal or viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion. In a preferred embodiment, the inflammation-mediated condition of the eye is uveitis. In another preferred embodiment, the inflammation-mediated condition of the eye is proliferative vitrioretinopathy (PVR).

The delivery systems are designed to release the glucocorticoid at therapeutic levels to the vitreous for a sustained period of time. In one embodiment, the implant delivers the agent to the vitreous in an amount sufficient to reach a concentration equivalent to at least about 0.05 $\mu$g/ml dexamethasone within about 48 hours. In other embodiments, the implant delivers the agent to the vitreous in an amount sufficient to reach a concentration equivalent to at least about 0.06 $\mu$g/ml, at least about 0.07 $\mu$g/ml, at least about 0.08 $\mu$g/ml, at least about 0.1 $\mu$g/ml, at least about 0.125 $\mu$g/ml, at least about 0.15 $\mu$g/ml dexamethasone within about 48 hours.

In another embodiment, the implant delivers the agent to the vitreous in an amount sufficient to reach a concentration equivalent to at least about 0.2 $\mu$g/ml dexamethasone within about 6 hours. In other embodiments, the implant delivers the agent to the vitreous in an amount sufficient to reach a concentration equivalent to at least about 0.3 $\mu$g/ml, at least about 0.5 $\mu$g/ml, at least about 0.75 $\mu$g/ml, at least about 1.0 $\mu$g/ml, at least about 2.0 $\mu$g/ml dexamethasone within about 4 hours, within about 6 hours, within about 8 hours, within about 10 hours, within about 24 hours.

A concentration equivalent to at least about 0.01 $\mu$g/ml, at least about 0.02 $\mu$g/ml, at least about 0.03 $\mu$g/ml, at least about 0.05 $\mu$g/ml, at least about 0.07 $\mu$g/ml dexamethasone may be maintained for an extended period of time (e.g., at least about three weeks.) The preferred concentration levels of drug in the vitreous may vary according to the inflammatory mediated condition being treated. For treating uveitis, a concentration equivalent of at least about 0.01 to 0.1 $\mu$g/ml dexamethasone is preferred.

In one embodiment, said concentration is maintained for least about four weeks. In other embodiments, said concentration is maintained for at least about five weeks, at least about six weeks, at least about seven weeks, at least about eight weeks, at least about nine weeks, at least about 10 weeks, at least about 12 weeks. The preferred duration of drug release may be determined by the inflammatory mediated condition being treated. For treating uveitis, a drug release duration of at least about three weeks is preferable, more preferably at least about four weeks. In one embodiment, more than one implant may be sequentially implanted into the vitreous in order to maintain drug concentrations for even longer periods.

The implants may be inserted into the eye by a variety of methods, including placement by forceps or by trocar following making a 2–3 mm incision in the sclera. The method of placement may influence the drug release kinetics. For example, implanting the device with a trocar may result in placement of the device deeper within the vitreous than placement by forceps, which may result in the implant being closer to the edge of the vitreous. The location of the implanted device may influence the concentration gradients of drug surrounding the device, and thus influence the release rates (e.g., a device placed closer to the edge of the vitreous will result in a slower release rate).

Implants for Use in Treating Inflammatory-Mediated Conditions

The formulation of the implants for use in the invention may vary according to the preferred drug release profile, the particular glucocorticoid used, the condition being treated, and the medical history of the patient.

The implants of the invention are formulated with particles of the steroidal anti-inflammatory agent entrapped within the bioerodible polymer matrix. Release of the agent is achieved by erosion of the polymer followed by exposure of previously entrapped agent particles to the vitreous, and subsequent dissolution and release of agent. The release kinetics achieved by this form of drug release are different than that achieved through formulations which release drug through polymer swelling, such as with hydrogels such as methylcellulose. In that case, the drug is not released through polymer erosion, but through polymer swelling, which releases drug as liquid diffuses through the pathways exposed. The parameters which determine the release kinetics include the size of the drug particles, the water solubility of the drug, the ratio of drug to polymer, the method of manufacture, the surface area exposed, and the erosion rate of the polymer.

Preferably, the steroidal anti-inflammatory agent is selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide. In a preferred embodiment, the steroidal anti-inflammatory agent is selected from the group consisting of cortisone, dexamethasone, hydrocortisone, methylprednisolone, prednisolone, prednisone, and triamcinolone. In a more preferred embodiment, the steroidal anti-inflammatory agent is dexamethasone. In another embodiment, the bioerodible implant comprises more than one steroidal anti-inflammatory agent.

The implants may further comprise one or more additional therapeutic agents, such as antimetabolites and/or antibiotics. Antimetabolites include, but are not limited to, folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), and pyrimidine analogs (e.g., ancitabine, azacitidine, 6-azauridine, carmofur, cytarabine, doxifluridine, emitefur, enocitabine, floxuridine, fluorouracil, gemcitabine, tegafur). Specific antibiotics include, but are not limited to:

Antibacterial antibiotics:

Aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Synthetic antibacterials:

2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofuirantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, $n^4$-β-d-glucosylsulfanilamide, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, $n^4$-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibomol).

Antifungal antibiotics:

Polyenes (e.g., amphotericin b, candicidin, dermostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Synthetic antifungals:

Allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Antineoplastic:

Antibiotics and analogs (e.g., aclacinomycins, actinomycin $f_1$, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

The steroidal anti-inflammatory agent is preferably from about 10 to 90% by weight of the implant. More preferably, the agent is from about 50 to about 80% by weight of the implant. In a preferred embodiment, the agent comprises about 50% by weight of the implant. In a particularly preferred embodiment, the agent comprises about 70% by weight of the implant.

The implants are preferably monolithic, i.e. having the glucocorticoid homogenously distributed through the polymeric matrix. The selection of the polymeric composition to be employed will vary with the desired release kinetics, patient tolerance, the nature of the disease to be treated and the like. Characteristics of the polymers will include biodegradability at the site of implantation, compatibility with the agent of interest, ease of encapsulation, water insolubility, and the like. Preferably, the polymeric matrix will not be fully degraded until the drug load has been released. The polymer will usually comprise at least about 10, more usually at least about 20 weight percent of the implant.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked, usually not more than lightly cross-linked, generally less than 5%, usually less than 1%. For the most part, besides carbon and hydrogen, the polymers will include oxygen and nitrogen, particularly oxygen. The oxygen may be present as oxy, e.g., hydroxy or ether, carbonyl, e.g., non-oxo-carbonyl, such as carboxylic acid ester, and the like. The nitrogen may be present as amide, cyano and amino. The biodegrable polymers set forth in Heller, Biodegradable Polymers in Controlled Drug Delivery, in: CRC Critical Reviews in Therapeutic Drug Carrier Systems, Vol. 1. CRC Press, Boca Raton, Fla. (1987), may be used.

Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The % of polylactic acid in the polylactic acid polyglycolic acid (PLGA) copolymer can be 0–100%, preferably about 15–85%, more preferably about 35–65%. In a particularly preferred embodiment, a 50/50 PLGA copolymer is used. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. The size of the polymer particles is preferably about 1–100 μm in diameter, more preferably about 5–50 μm in diameter, more preferably about 9–12 μm in diameter, still more preferably about 10 μm in diameter.

Among the polysaccharides of interest are calcium alginate, and functionalized celluloses, particularly carboxymethylcellulose esters characterized by being biodegradable, water insoluble, a molecular weight of about 5 kD to 500 kD, etc.

Additionally, release modulators such as those described in U.S. Pat. No. 5,869,079 may be included in the implants. The amount of release modulator employed will be dependent on the desired release profile, the activity of the modulator, and on the release profile of the glucocorticoid in the absence of modulator.

Other agents may be employed in the formulation for a variety of purposes. For example, buffering agents and preservatives may be employed. Water soluble preservatives which may be employed include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents may be present in individual amounts of from about 0.001 to about 5% by weight and preferably about 0.01 to about 2%. Suitable water soluble buffering agents that may be employed are sodium carbonate, sodium borate, sodium phosphate, sodium acetate, sodium bicarbonate, etc., as approved by the FDA for the desired route of administration. These agents may be present in amounts sufficient to maintain a pH of the system of between 2 to 9 and preferably 4 to 8. As such the buffering agent may be as much as 5% on a weight to weight basis of the total composition. Electrolytes such as sodium chloride and potassium chloride may also be included in the formulation. Where the buffering agent or enhancer is hydrophilic, it may also act as a release accelerator. Hydrophilic additives act to increase the release rates through faster dissolution of the material surrounding the drug particles, which increases the surface area of the drug exposed, thereby increasing the rate of drug bioerosion. Similarly, a hydrophobic buffering agent or enhancer dissolve more slowly, slowing the exposure of drug particles, and thereby slowing the rate of drug bioerosion.

The proportions of glucocorticoid, polymer, and any other modifiers may be empirically determined by formulating several implants with varying proportions. A USP approved method for dissolution or release test can be used to measure the rate of release (USP 23; NF 18 (1995) pp. 1790–1798). For example, using the infinite sink method, a weighed sample of the drug delivery device is added to a measured volume of a solution containing 0.9% NaCl in water, where the solution volume will be such that the drug concentration is after release is less than 5% of saturation. The mixture is maintained at 37° C. and stirred slowly to maintain the implants in suspension. The appearance of the dissolved drug as a function of time may be followed by various methods known in the art, such as spectrophotometrically, HPLC, mass spectroscopy, etc. until the absorbance becomes constant or until greater than 90% of the drug has been released.

The release kinetics of the drug delivery devices of the invention are dependent in part on the surface area of the devices. Larger surface area exposes more polymer to the vitreous, causing faster erosion and dissolution of the drug particles entrapped by the polymer. The size and form of the implant can be used to control the rate of release, period of treatment, and drug concentration at the site of implantation. Larger implants will deliver a proportionately larger dose, but depending on the surface to mass ratio, may have a slower release rate. The implants may be particles, sheets, patches, plaques, films, discs, fibers, microcapsules and the like and may be of any size or shape compatible with the selected site of insertion, as long as the implants have the desired release kinetics. Preferably, the implant to be inserted is formulated as a single particle. Preferably, the implant will not migrate from the insertion site following implantation. The upper limit for the implant size will be determined by factors such as the desired release kinetics, toleration for the implant, size limitations on insertion, ease of handling, etc. The vitreous chamber is able to accommodate relatively large implants of varying geometries, having diameters of 1 to 3 mm. In a preferred embodiment, the implant is a cylindrical pellet (e.g., rod) with dimensions of about 2 mm×0.75 mm diameter. The implants will also preferably be at least somewhat flexible so as to facilitate both insertion of the implant in the vitreous and accommodation of the implant. The total weight of the implant is preferably about 250–5000 $\mu$g, more preferably about 500–1000 $\mu$g. In one embodiment, the implant is about 500 g. In a particularly preferred embodiment, the implant is about 1000 $\mu$g.

In a preferred embodiment, a solid bioerodible implant for treating an inflammation-mediated condition of the eye is provided, consisting essentially of: dexamethasone particles entrapped within a polylactic acid polyglycolic acid (PLGA) copolymer, wherein the implant comprises about 70 percent by weight of dexamethasone and about 30 percent by weight of PLGA, wherein the total mass of the implant is about 800–1100 $\mu$g, and wherein the implant releases at least about 10% of the drug load within 1 week when measured under infinite sink conditions in vitro. In a more preferred embodiment, the total mass of the implant is about 1000 $\mu$g. In other embodiments, the implant releases at least about 15%, at least about 20%, at least about 25%, at least about 30%, at least about 35%, of the drug load within 1 week when measured under infinite sink conditions in vitro. In other embodiments, the implant releases at least about 15%, at least about 20%, at least about 30%, at least about 40%, at least about 50%, of the drug load within 2 weeks when measured under infinite sink conditions in vitro.

Methods for Making the Implants of the Invention

Various techniques may be employed to produce the implants. Useful techniques include phase separation methods, interfacial methods, extrusion methods, compression methods, molding methods, injection molding methods, heat press methods and the like.

Choice of the technique, and manipulation of the technique parameters employed to produce the implants can influence the release rates of the drug. Room temperature compression methods result in an implant with discrete microparticles of drug and polymer interspersed. Extrusion methods result in implants with a progressively more homogenous dispersion of the drug within the polymer, as the production temperature is increased. When using extrusion methods, the polymer and drug are chosen to as to be stable at the temperatures required for manufacturing, usually at least about 85° C. Extrusion methods use temperatures of about 25° C. to about 150° C., more preferably about 65° C. to about 130° C. Generally, compression methods yield implants with faster release rates than extrusion methods, and higher temperatures yield implants with slower release rates.

In a preferred embodiment, compression methods are used to produce the implants of the invention. Preferably, compression methods use pressures of 50–150 psi, more preferably about 70–80 psi, even more preferably about 76 psi, and use temperatures of about 0° C. to about 115° C., more preferably about 25° C. In another preferred embodiment, extrusion methods are used. Preferably, implants produced by extrusion methods are heated to a temperature range of about 60° C. to about 150° C. for drug/polymer mixing, more preferably about 130° C., for a time period of about 0 to 1 hour, 0 to 30 minutes, 5–15 minutes, preferably about 10 minutes, preferably about 0 to 5 min. Preferably, the implants are then extruded at a temperature of about 60° C. to about 130° C., more preferably about 75° C.

Kits for the Administration of the Implants

In another aspect of the invention, kits for treating an inflammation-mediated condition of the eye are provided, comprising: a) a container comprising a bioerodible implant comprising dexamethasone and polylactic acid polyglycolic acid (PLGA) copolymer in a ratio of about 70/30; and b) instructions for use.

The invention is further illustrated by the following nonlimiting examples.

EXAMPLES

Example 1

Manufacture and In vitro Testing of Bioerodible Dexamethasone Posterior Segment Drug Delivery System (DEX PS DDS®)

2100 mg of dexamethasone powder (Upjohn) (particle sizes less than 10 $\mu$m in diameter) were mixed with 900 mg of 50/50 polylactic acid polyglycolic acid (PLGA) (particle sizes approximately 9–12 $\mu$m in diameter) at ambient temperature. A small Teflong tube was filled with 900–1100 $\mu$g of the above mixture, and placed directly on the die cavity. The powder was pushed out of the tubing into the die cavity with a stainless steel wire and the tube and wire were removed from the die. The powder was pressed using a tablet press (approximately 76 psi), ejected with the ejector switch, and removed with tweezers. The resulting pellet was approximately 2 mm×0.75 mm.

Release of dexamethasone from the DEX PS DDS® system was measured. One DDS was placed in a glass vial filled with receptor medium (0.9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, the glass vial was placed into a shaking water bath at 37° C. Samples were taken for HPLC analysis from the vial at defined time points. The HPLC method was as described in USP 23(1995) pp.1791–1798. The concentration values were used to calculate the cumulative release data, as shown in Table 1.

TABLE 1

DEX PS DDS ® In vitro Release

| Day | % Total Release |
|---|---|
| 1 | 10.1 |
| 2 | 16.4 |
| 7 | 39.4 |
| 14 | 55.5 |
| 21 | 69.3 |
| 28 | 80.7 |
| 35 | 88.1 |

Table 1 shows an almost linear in vitro release of dexamethasone over a one month period of time.

Example 2
In vivo Testing of DEX PS DDS® in Rabbits

One DEX PS DDS® per eye was implanted into the vitreous of four rabbits with forceps. The in vivo vitreous concentrations of dexamethasone in each of the four eyes were monitored by vitreous sampling. For example, at day 2 the concentrations measured were 0.03 µg/ml, 0.1 µg/ml, 0.33 µg/ml and 0.19 µg/ml. The concentrations in each of the four eyes were measured on days 2, 7, 21, 28 and 35; the average results are summarized in Table 2. The volume of rabbit eyes is approximately 60–70% percent that of human eyes.

TABLE 2

In vivo concentrations of dexamethasone (DDS placed with forceps)

| Day | µg/ml |
|---|---|
| 2 | 0.16 ± 0.13 |
| 7 | 0.15 ± 0.16 |
| 21 | 0.08 ± 0.07 |
| 28 | 0.005 ± 0.01 |
| 35 | 0.037 ± 0.03 |

The same DDS was tested in vivo in rabbits, wherein the DDS was placed to a depth of about 5–10 mm in the vitreous with trocar. The levels of dexamethasone in the vitreous are shown in Table 3.

| Animal #\ day | DDS wt. ug | Dex wt. ug | Dex ug/mL | | | | | |
|---|---|---|---|---|---|---|---|---|
| | | | 2 | 7 | 14 | 21 | 28 | 35 |
| 21427-D | 990 | 693 | 2.29 | | | | | |
| 21427-S | 1023 | 715.1 | 1.56 | | | | | |
| 21433-D | 804 | 562.8 | 1.2 | | | | | |
| 21433-S | 1057 | 739.9 | 0.77 | | | | | |
| 21428-D | 1003 | 702.1 | | 9.26 | | | | |
| 21428-S | 1025 | 717.5 | | 0.35 | | | | |
| 21434-D | 863 | 604.1 | | 3.31 | | | | |
| 21434-S | 1106 | 774.2 | | 0.84 | | | | |
| 21429-D | 1013 | 709.1 | | | n/a | | | |
| 21429-S | 927 | 648.9 | | | 0.19 | | | |
| 21435-D | 1104 | 772.8 | | | 0.43 | | | |
| 21435-S | 941 | 658.7 | | | 0.11 | | | |
| 21432-D | 860 | 692 | | | | 0.43 | | |
| 21432-S | 941 | 685.7 | | | | 1.72 | | |
| 21436-D | 1010 | 707 | | | | 0.31 | | |
| 21436-S | 1054 | 737.8 | | | | 0.13 | | |
| 21431-D | 996 | 697.2 | | | | | 0.52 | |
| 21431-S | 918 | 642.6 | | | | | 1.15 | |
| 21437-D | 1049 | 732.9 | | | | | 0.19 | |
| 21437-D | 1075 | 752.5 | | | | | 0.48 | |
| 21430-D | 994 | 695.8 | | | | | | 0.06 |
| 21430-S | 1086 | 760.2 | | | | | | 0.18 |
| 21438-D | 974 | 681.8 | | | | | | 0.03 |
| 21438-S | 831 | 581.7 | | | | | | 8.35 |
| Ave. | 985.17 | 694.43 | 1.46 | 3.44 | 0.24 | 0.65 | 0.59 | 2.16 |

*Unable to determine due to insufficient sample

The data indicate that the DEX PS DDS® releases dexamethasone to the vitreous in concentrations above 0.01 µg/ml for an extended period of time. Further, the data indicate that placement of the device with trocar results in much higher levels of drug release than with placement with forceps, most likely due to placement of the device deeper within the vitreous. The data at two, four, six, and 24 hours in Table 3 shows an initial spike of drug release.

Example 3
Treatment of Severe Uveitis in Human Patients with DEX PS DDS®

Three eyes of two patients (ages 5 and 55 years) with severe progressive uveitis were treated with the DEX PS DDS®. The use of the DEX PS DDS® in compassionate and emergency use situations was conducted under an investigative new drug application (IND) with the U.S. F.D.A. A written informed consent was obtained from the participating patients.

Subjects in this study underwent pars plana vitrectomy. Immediately after the vitrectomy, the DEX PS DDS® was inserted into the vitreous cavity through the pars plana. The DDS pellet appeared to remain in the location where it was placed, and released the drug over at least approximately 4–5 weeks.

TABLE 3

In vivo concentrations of dexamethasone (DDS placed with trocar)

| Hours | Sample ID | | | | | | | | Avg | SD |
|---|---|---|---|---|---|---|---|---|---|---|
| | 5293-D | 5295 = D | 5293-S | 5295-S | 5304-D | 5306-D | 5304-S | 5306-S | | |
| | Sample Conc., ug/ml | | | | | | | | | |
| 2 | 0.56 | 3.007 | | | | | | | 1.82 | 1.77 |
| 4 | | | 5.48 | 6.95 | | | | | 6.22 | 1.04 |
| 6 | | | | | 2.08 | 5.15 | | | 3.62 | 2.17 |
| 24 | | | | | | | 2.33 | 2.69 | 2.51 | 0.25 |

Patient #1 was a 55-year-old female who initially presented with optic neuritis in 1990. This patient subsequently developed recurrent posterior uveitis secondary to inflammatory polyarthritis. Response to systemic and periocular steroid treatment was intermittent. Methotrexate and cyclosporine were found to be effective; however, these drugs induced severe side effects. Methotrexate caused elevated liver enzymes and pancreatitis. The patient developed pustular dermatitis with cyclosporine treatment. Cytoxan was subsequently used, both intravenously and orally, with satisfactory initial results. Later, the inflammatory polyarthritis was controlled with Gold injections. The patient's Type I diabetes was well controlled and the pancreatitis resolved.

The patient was referred to us in September 1998 for further evaluation and treatment of uveitis due to progressive visual loss and lack of response to conventional medications. A vitrectomy had been performed on her left eye several years earlier for treatment of uveitis. Visual acuity in both eyes was counting fingers. Intraocular pressure in both eyes was 20 mm Hg. Slit larnp exam of the right anterior chamber revealed trace flare and 1–5 cells. Examination of the left anterior chamber revealed no flare and 8–9 cells. A mild nuclear sclerotic cataract was present in the right eye and a moderate one was noted in the left eye. In the anterior vitreous of the right eye, 50–100 fine cells were present. There were 6–7 cells in the left anterior vitreous.

On ophthalmoscopy of the right eye, the vitreous was hazy and a poor view was obtained. It was possible to see a peripapillary scar and numerous histoplasmosis type retinal scars 360° from the posterior pole out to the periphery. In the left eye, the vitreous was not as hazy and the retina appearance was very similar to that of the right eye. The right eye was selected for initial treatment due to its more acute involvement and the more severe inflammatory response.

In October 1998, a standard three port system pars plana vitrectomy was performed and the DEX PS DDSO was inserted through the pars plana. At the end of surgery, the patient received periocular celestone suspension 1 cc (β-methadone sodium phosphate/β-methazone acetate, Schering-Plough) and periocular gentamicin 0.1 cc (Abbott Laboratories). Topical medications consisting of Tobradex® (tobramycin/dexamethasone, Alcon Labs) and Cyclogyl® 1% drops (cyclopentolate HCl, Alcon Labs) q.i.d. were prescribed. The retina was clearly seen for the first time during surgery after removal of the vitreous. There was a peripapillary scar and numerous healed histoplasmosis type scars 360° from the posterior pole to the periphery. In addition, there were several small retinal hemorrhages that appeared to be consistent with diabetic retinopathy. No active inflammatory retinitis or choroiditis was seen. A mild amount of epiretinal gliosis was present at six o'clock in the mid-periphery. There was no evidence of snowbanking or snowball opacities.

The first (right) eye of patient #1 improved from counting fingers to 20/200 on the first day postoperatively. The best vision was 20/40 at six months. One year acuity was 20/50 and at the last visit (16 months) the vision was 20/60 (Table 3).

TABLE 4

Patient 1: Right Eye Visual Acuity

|  | Visual Acuity |
|---|---|
| PreOp | CF |
| Day 1 | 20/200 |
| Month 1 | 20/200 |
| Month 2 | 20/80 |

TABLE 4-continued

Patient 1: Right Eye Visual Acuity

|  | Visual Acuity |
|---|---|
| Month 3 | 20/60 |
| Month 4 | 20/40 |
| Month 5 | 20/50 |
| Month 16 | 20/60 |

Postoperatively, anterior chamber flare varied between 0 and trace and cells varied between 1 and 6. Vitreous flare varied between 0 and trace. Vitreous cells varied between 0 and 20.

On ophthalmoscopy, the vitreous and retina were found to remain completely quiet. The DEX PS DDS® implant was resorbed at approximately five weeks. The retinal hemorrhages disappeared. There was no detectable increase in the patient's cataract. Fluorescein angiography did not reveal any evidence of macular edema. Present eye medications consist of Acular® (ketorolac promethamine 0.5%, Allergan) drops q.i.d.

After it was determined that favorable results were achieved in the right eye, the patient received the same treatment for the left eye in April 1999. The left eye presented very similarly to the right eye, other than a more significant cataract and the uveitis being more chronic in nature. Notably, a pars plana vitrectomy had been performed on this eye for this condition 3 years previously.

The second (left) eye of patient #1 initially improved to a visual acuity of 20/400 (3 months postoperatively), but later returned to counting fingers (7.5 months). This decline in visual acuity appeared to be secondary to progression of the cataract. Postoperatively (first 10 months), on slit lamp examination, anterior chamber flare varied from 0 to moderate and cells varied from 0 to >30. Vitreous flare varied from 0 to severe and vitreous cells varied from 0 to >250. On the last visit (11 months), there was no AC flare or cells, and vitreous detail was not observed due to cataract. There had been no vitreous flare or cells detected on the previous visit (10 months). Visual acuity at 11 months was counting fingers. Present eye medications consist of Acular® drops q.i.d.

Patient #2 is a 5-year-old male with an eight month history of bilateral pars planitis. The right eye was mild and stable, but the left eye was progressive and severe with only transient response to topical and subtenon steroids. This was an idiopathic uveitis. The patient developed complications in the left eye including decreased vision to 20/200, a posterior subcapsular cataract, band keratopathy, and glaucoma with intraocular pressures in the low 30's. There was mild flare and 20 cells in the anterior chamber.

The anterior vitreous was very prominent and the cells were too numerous to count. On ophthalmoscopy, the patient was found to have snowball vitreous opacities, snowbanking, and peripheral retinoschisis or a low retinal detachment. Multiple uveitis consultations offered treatment choices of systemic steroids, systemic antimetabolites, and pars plana vitrectomy. Because of the patient's young age and potential side effects of systemic treatments, it was elected to perform a pars plana vitrectomy. The surgery was carried out uneventfully in September 1999. The treatment consisted of a pars plana vitrectomy, insertion of DEX PS DDS®, and transconjunctival cryopexy.

Patient #2 had a one day postoperative visual acuity of 20/400 and the best vision was 20/70 (Table 4).

TABLE 5

Patient 2: Left Eye Visual Acuity

|  | Visual Acuity |
|---|---|
| PreOp | 20/200 |
| Month 1 | 20/70 |
| Month 2 | 20/100 |
| Month 3 | 20/70 |
| Month 4 | 20/80 |
| Month 5 | 20/100 |
| Month 6 | 20/80 |

Visual acuity at five months decreased to 20/100 secondary to progression of the posterior subcapsular cataract. On slit lamp examination, anterior chamber flare varied between 0 to mild and cells varied from 0 to 4. Vitreous flare was 0 and vitreous cells varied from 0 to 10. On ophthalmoscopy, a mild amount of residual snowballs and snowbanking was evident. The peripheral retinal detachment/schisis healed well and was flat. The eye responded very well with the exception of intraocular pressure. Pressures were in the teens up to the 20's in the immediate postoperative period, and after two months the pressure went up to 44 mm Hg. A glaucoma consultation was obtained and it was concluded that the intraocular pressure increase was due to the topical antibiotic steroid combination drops used postoperatively. The medications were terminated and the patient was prescribed topical anti-glaucoma medication. The last postoperative pressure measurement (6 months) was 13 mm Hg. There is no evidence of damage to the optic nerve. Present medications consist of Timoptic® 0.25% (timolol maleate, Falcon Pharmaceuticals), Acular®, and Vexol® 1% (rimexolone, Alcon Labs) all b.i.d. Outcomes for these two patients suggest that DEX PS DDS(® may be very effective in the treatment of severe uveitis. It appears that the DEX PS DDS® is well tolerated, and that the one month drug delivery system can be effective over a much longer period of time in treating these chronic uveitis patients.

Example 4
Treatment of Severe and Recalcitrant Uveitis in Human Patients with DEX PS DDS®

Four eyes of 4 patients who have had failed treatments for severe uveitis were treated with the DEX PS DDS®. Subjects in this study underwent a standard 3 port pars plana vitrectomy. Immediately after the vitrectomy, the DEX PS DDS® was inserted into the vitreous cavity through the pars plana. The DDS pellet appeared to remain in the location where it was placed, and released the drug over approximately 1 month.

Three patients had a single procedure with DEX PS DDS® insertion and 1 patient had a second DEX PS DDS® insertion when surgery was required from complications of the disease. All patients have shown a remarkable response to the medication and vision in all patients has improved. The beginning vision was as low as counting fingers only and the improvement has been as high as 20/30. With 2–22 months follow up all patients have responded positively and there have been no new recurrences. The patient who had 2 insertions has shown complete regression of the disease.

Example 5
Use of DEX PS DDS® in the Treatment of Recurrent Retinal Detachment

The effect of DEX PS DDS® as an adjunct in the treatment of recurrent retinal detachments associated with PVR was evaluated. Six eyes of six patients with 2–4 previous retinal procedures and who had recurrence due to PVR were treated with DEX PS DDS®, which was inserted into the vitreous cavity after a standard 3 port pars plana vitrectomy with membrane peeling, endolaser, and air-fluid-gas or silicone oil exchange, with or without a scleral buckle.

Four patients had surgery with reattachment with one operation. Two patients had a second procedure due to initial incomplete removal of the existing PVR. With the second procedure the retina of one patient has remained attached. The second patient has developed recurrent PVR and re-detachment and will undergo further surgery. With 3–13 months follow-up five retinas were attached with no new PVR.

The DEX PS DDS® appeared to be very effective in the treatment of PVR related retinal detachments.

Example 6
Manufacture and In vitro Testing of 50/50 Dexamethasone/PLGA Posterior Segment Drug Delivery System 2.5 g of PLGA (particle sizes approximately 9–12 µm in diameter) were placed in a mixing vessel. The vessel was placed in the oven (130° C.) for ten minutes. 2.5 g of dexamethasone (particle sizes less than approximately 10 µm in diameter) were added to the vessel, and the vessel was returned to the oven for 10 minutes. The PLGA/dexamethasone mixture was mixed well, the blend loaded into a barrel, and 650–790 µm diameter filaments extruded. The resulting filaments were cut into lengths of approximately 0.94 and 1.87 mm for the 500 µg and 1000 µg formulations, respectively.

Release of dexamethasone from the 50/50 dexamethasone/PLGA DDS formulations were measured. One DDS was placed in a glass vial filled with receptor medium (0.9% NaCl in water). To allow for "infinite sink" conditions, the receptor medium volume was chosen so that the concentration would never exceed 5% of saturation. To minimize secondary transport phenomena, e.g. concentration polarization in the stagnant boundary layer, the glass vial was placed into a shaking water bath at 37° C. Samples were taken for HPLC analysis from the vial at defined time points. The HPLC method was as described in USP 23(1995) pp.1791–1798. The concentration values were used to calculate the cumulative release data, as shown in Table 6.

TABLE 6

In vitro release of 50% Dex-PS (0.5 mg formulation)

| Day | Dex ug Release/day | % Total release |
|---|---|---|
| 50% Dex PS 0.5 mg system replicate 1 | | |
| 1 | 3.00 | 1.41 |
| 7 | 1.99 | 7.93 |
| 13 | 0.90 | 13.43 |
| 20 | 1.79 | 30.21 |
| 27 | 1.54 | 49.77 |
| 34 | 1.93 | 80.52 |
| 41 | 0.24 | 85.05 |
| 48 | 0.24 | 90.38 |
| 55 | 0.10 | 93.00 |
| 62 | 0.15 | 97.44 |
| 69 | 0.07 | 99.84 |
| 76 | 0.07 | 102.25 |
| 50% Dex PS 0.5 mg system replicate 2 | | |
| 1 | 6.00 | 2.17 |
| 7 | 1.66 | 6.38 |
| 13 | 0.99 | 11.05 |

TABLE 6-continued

In vitro release of 50% Dex-PS (0.5 mg formulation)

| Day | Dex ug Release/day | % Total release |
|---|---|---|
| 20 | 1.21 | 19.82 |
| 27 | 2.29 | 42.23 |
| 34 | 2.34 | 71.05 |
| 41 | 0.44 | 77.54 |
| 48 | 0.29 | 82.61 |
| 55 | 0.14 | 85.34 |
| 62 | 0.20 | 89.80 |
| 69 | 0.10 | 92.21 |
| 76 | 0.06 | 84.38 |
| 50% Dex PS 0.5 mg system replicate 3 | | |
| 1 | 5.70 | 3.27 |
| 7 | 1.11 | 7.71 |
| 13 | 0.83 | 13.83 |
| 20 | 0.05 | 14.47 |
| 27 | 1.63 | 39.63 |
| 34 | 1.52 | 69.26 |
| 41 | 0.21 | 74.10 |
| 48 | 0.19 | 79.23 |
| 55 | 0.08 | 81.69 |
| 62 | 0.14 | 86.58 |
| 69 | 0.07 | 89.46 |
| 76 | 0.06 | 92.26 |

TABLE 7

In vitro release of 50% Dex-PS (1 mg formulation)

| Day | Dex ug Release/day | % Total release |
|---|---|---|
| 50% Dex PS 1 mg system replicate 1 | | |
| 1 | 6.90 | 1.28 |
| 7 | 3.48 | 5.78 |
| 13 | 1.93 | 10.43 |
| 20 | 3.46 | 23.22 |
| 27 | 3.74 | 41.89 |
| 34 | 3.94 | 66.83 |
| 41 | 1.79 | 80.17 |
| 48 | 1.28 | 91.49 |
| 55 | 0.21 | 93.59 |
| 62 | 0.24 | 96.39 |
| 69 | 0.11 | 97.85 |
| 76 | 0.09 | 99.11 |
| 50% Dex PS 1 mg system replicate 2 | | |
| 1 | 3.90 | 0.71 |
| 7 | 2.26 | 3.62 |
| 13 | 1.66 | 7.57 |
| 20 | 3.14 | 19.09 |
| 27 | 4.32 | 40.48 |
| 34 | 4.06 | 65.77 |
| 41 | 1.61 | 77.90 |
| 48 | 1.34 | 89.70 |
| 55 | 0.19 | 91.60 |
| 62 | 0.23 | 94.18 |
| 69 | 0.10 | 95.50 |
| 76 | 0.09 | 96.78 |
| 50% Dex PS 1 mg system replicate 3 | | |
| 1 | 4.50 | 0.91 |
| 7 | 2.16 | 3.98 |
| 13 | 1.69 | 8.42 |
| 20 | 1.25 | 13.48 |
| 27 | 3.88 | 34.67 |
| 34 | 3.53 | 58.97 |
| 41 | 1.85 | 74.28 |
| 48 | 0.88 | 82.85 |
| 55 | 0.19 | 84.94 |
| 62 | 0.26 | 88.15 |
| 69 | 0.11 | 89.75 |
| 76 | 0.10 | 91.26 |

Example 7

In vivo Testing of 50/50 Dexamethasone/PLGA 1 mg Formulations in Rabbits

One 50/50 dexamethasone/PLGA 1 mg formulation DDS per eye was implanted into the vitreous of 6 rabbits using a trocar. The DDS was loaded into the trocar, a hole was punched through the sclera, the trocar inserted through the hole, and the trocar plunger depressed to insert the DDS into the vitreous. In vivo vitreous concentrations of dexamethasone were monitored, as shown in Table 8.

TABLE 8

In vivo vitreous concentrations of dexamethasone

| Hours | Sample ID | | | | | | | | Avg | SD |
|---|---|---|---|---|---|---|---|---|---|---|
| | 5293-D | 5295 = D | 5293-S | 5295-S | 5304-D | 5306-D | 5304-S | 5306-S | | |
| | Sample Conc., ug/ml | | | | | | | | | |
| 2 | 1.38 | 1.69 | | | | | | | 1.54 | 0.22 |
| 4 | | | 2.16 | 0.96 | | | | | 0.47 | 0.37 |
| 6 | | | | | 0.73 | 0.21 | | | 0.47 | 0.37 |
| 24 | | | | | | | 0.57 | 0.74 | 0.66 | 0.12 |

| | Dex ug/mL | | | | |
|---|---|---|---|---|---|
| Animal #\day | 7 | 21 | 35 | 49 | 63 |
| 2953-D | 0.5 | | | 0.58 | |
| 2953-S | 0.11 | | | 0.69 | |
| 2952-D | 0.13 | | | 1.2 | |
| 2952-S | 0.12 | | | 0.55 | |
| 2946-D | | 0.19 | | | 2.55 |
| 2946-S | | *3 | | | 0.14 |

TABLE 8-continued

In vivo vitreous concentrations of dexamethasone

| | | | | | |
|---|---|---|---|---|---|
| 2949-D | | *5.44 | | | 0.28 |
| 2949-S | | 0.0248 | | | 0.01 |
| 2982-D | | | 1.087 | | |
| 2982-S | | | 0.058 | | |
| 2983-D | | | 0.018 | | |
| 2983-S | | | 0.045 | | |
| Ave. | 0.22 | 2.16 | 0.30 | 0.76 | 0.75 |

*High level was due to the surgical artifact

The data indicate that the 50/50 dexamethasone/PLGA DDS releases dexamethasone to the vitreous in concentrations above 0.01 µg/ml for an extended period of time. The data at two, four, six, and 24 hours in Table 8 shows an initial spike of drug release, due to drug which is unencapsulated by the delivery system.

The 100–120 µg 50/50 PLGA/dexamethasone implant disclosed in U.S. Pat. No. 5,869,079 shows similar in vitro release kinetics to the 500 and 1000 µg 50/50 PLGA/dexamethasone implant disclosed herein. However, the previously disclosed implant would not provide drug concentrations in the vitreous at the levels described herein.

Modifications of the above described modes for carrying out the invention that are obvious to those of ordinary skill in the surgical, pharmaceutical, or related arts are intended to be within the scope of the following claims.

What is claimed is:

1. A method for treating an inflammation-mediated condition of the eye in an individual, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.05 µg/ml dexamethasone within about 48 hours and maintains a concentration equivalent to at least about 0.03 µg/ml dexamethasone for at least about three weeks.

2. The method according to claim 1, wherein the steroidal anti-inflammatory agent is selected from the group consisting of cortisone, dexamethasone, hydrocortisone, methylprednisolone, prednisolone, prednisone, and triamcinolone.

3. The method according to claim 1, wherein the steroidal anti-inflammatory agent is dexamethasone.

4. The method according to claim 1, wherein the implant delivers the agent to the vitreous in an amount sufficient to reach a concentration equivalent to at least about 0.1 µg/ml dexamethasone within about 48 hours and maintains a concentration equivalent to at least about 0.03 µg/ml dexamethasone for at least about three weeks.

5. The method according to claim 1, wherein said concentration is maintained for least about four weeks.

6. The method according to claim 1, wherein the steroidal anti-inflammatory agent comprises about 50 to about 80 weight percent of the implant.

7. The method according to claim 6, wherein the steroidal anti-inflammatory agent comprises about 70% by weight of the implant.

8. The method according to claim 1, wherein the bioerodible polymer is a polyester.

9. The method according to claim 8, wherein the bioerodible polymer is polylactic acid polyglycolic acid (PLGA) copolymer.

10. The method according to claim 1, wherein the inflammation-mediated condition of the eye is selected from the group consisting of uveitis, macular edema, acute macular degeneration, retinal detachment, ocular tumors, fungal infections, viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion.

11. The method according to claim 10, wherein the inflammation-mediated condition of the eye is uveitis.

12. The method according to claim 10, wherein the inflammation-mediated condition of the eye is proliferative vitreoretinopathy (PVR).

13. The method according to claim 1, wherein the individual is a human.

14. A method for treating an inflammation-mediated condition of the eye in an individual, comprising: implanting a solid body into the vitreous of the eye, said body comprising particles of a steroidal anti-inflammatory agent entrapped within a bioerodible polymer, whereby said agent is delivered to the vitreous at a rate and for a time sufficient to reach a concentration equivalent to at least about 0.05 µg/ml dexamethasone within about 48 hours, and maintains a concentration equivalent to at least about 0.03 µg/ml dexamethasone for at least about three weeks.

15. A method for treating an inflammation-mediated condition of the eye in an individual, comprising: implanting into the vitreous of the eye a bioerodible implant comprising a steroidal anti-inflammatory agent and a bioerodible polymer, wherein the implant delivers the agent to the vitreous in an amount sufficient to reach a concentration equivalent to at least about 0.2 µg/ml dexamethasone within about 6 hours and maintains a concentration equivalent to at least about 0.01 µg/ml dexamethasone for at least about three weeks.

16. The method according to claim 15, wherein the steroidal anti-inflammatory agent is selected from the group consisting of cortisone, dexamethasone, hydrocortisone, methylprednisolone, prednisolone, prednisone, and triamcinolone.

17. The method according to claim 15, wherein the steroidal anti-inflammatory agent is dexamethasone.

18. The method according to claim 15, wherein the implant delivers the agent to the vitreous in an amount sufficient to reach a concentration equivalent to at least about 0.4 µg/ml dexamethasone within about 6 hours and maintains a concentration equivalent to at least about 0.01 µg/ml dexamethasone for at least about three weeks.

19. The method according to claim 15, wherein the implant delivers the agent to the vitreous in an amount sufficient to reach a concentration equivalent to at least about 0.2 µg/ml dexamethasone within about 6 hours and maintains a concentration equivalent to at least about 0.1 µg/ml dexamethasone for at least about three weeks.

20. The method according to claim 15, wherein said concentration is maintained for least about four weeks.

21. The method according to claim 15, wherein said concentration is maintained for least about six weeks.

22. The method according to claim 15, wherein the steroidal anti-inflammatory agent comprises about 50 to about 80 weight percent of the implant.

23. The method according to claim 22, wherein the steroidal anti-inflammatory agent comprises about 70% by weight of the implant.

24. The method according to claim 22, wherein the steroidal anti-inflammatory agent comprises about 50% by weight of the implant.

25. The method according to claim 15, wherein the bioerodible polymer is a polyester.

26. The method according to claim 25, wherein the bioerodible polymer is polylactic acid polyglycolic acid (PLGA) copolymer.

27. The method according to claim 15, wherein the inflammation-mediated condition of the eye is selected from the group consisting of uveitis, macular edema, acute macular degeneration, retinal detachment, ocular tumors, fungal infections, viral infections, multifocal choroiditis, diabetic uveitis, proliferative vitreoretinopathy (PVR), sympathetic opthalmia, Vogt Koyanagi-Harada (VKH) syndrome, histoplasmosis, and uveal diffusion.

28. The method according to claim 27, wherein the inflammation-mediated condition of the eye is uveitis.

29. The method according to claim 27, wherein the inflammation-mediated condition of the eye is proliferative vitreoretinopathy (PVR).

30. The method according to claim 15, wherein the individual is a human.

31. A method for treating an inflammation-mediated condition of the eye in an individual, comprising: implanting a bioerodible solid body into the vitreous of the eye, said body comprising particles of a steroidal anti-inflammatory agent entrapped within a bioerodible polymer, whereby said agent is delivered to the vitreous at a rate and for a time sufficient to reach a concentration equivalent to at least about 0.2 µg/ml dexamethasone within about 6 hours, and maintains a concentration equivalent to at least about 0.01 µg/ml dexamethasone for at least about three weeks.

32. A solid bioerodible implant for treating an inflammation-mediated condition of the eye, consisting essentially of: dexamethasone particles entrapped within a polylactic acid polyglycolic acid (PLGA) copolymer, wherein the dexamethasone makes up between about 50 percent by weight and about 80 percent by weight of the implant, and wherein the implant releases at least about 10% of the drug load within 1 week when measured under infinite sink conditions in vitro.

33. A solid bioerodible implant for treating an inflammation-mediated condition of the eye, the implant consisting essentially of: dexamethasone particles entrapped within a polyactic acid polyglycolic acid (PLGA) copolymer matrix, wherein the dexamethasone makes up between about 50 percent by weight and about 80 percent by weight of the implant, and wherein the implant releases at least about 15% of the dexamethasone within 2 weeks when measured under infinite sink conditions in vitro.

34. The solid bioerodible implant of claim 33, wherein the implant releases at least about 20% of the dexamethasone within 2 weeks when measured under infinite sink conditions in vitro.

35. The solid bioerodible implant of claim 34, wherein the implant releases at least about 40% of the dexamethasone within 2 weeks when measured under infinite sink conditions in vitro.

36. A method for treating an inflammation-mediated condition of the eye in an individual, comprising: implanting into the vitreous of the eye a bioerodible implant comprising a steroidal anti-inflammatory agent and a bioerodible polymer, wherein the implant releases at least about 15% of the steroidal anti-inflammatory agent within 2 weeks when measured under infinite sink conditions in vitro.

37. The method according to claim 36, wherein the implant releases at least about 20% of the steroidal anti-inflammatory agent within 2 weeks when measured under infinite sink conditions in vitro.

38. The method according to claim 37, wherein the implant releases at least about 40% of the steroidal anti-inflammatory agent within 2 weeks when measured under infinite sink conditions in vitro.

39. The method according to claim 10, wherein the inflammation-mediated condition of the eye is macular edema.

40. The method according to claim 27, wherein the inflammation-mediated condition of the eye is macular edema.

41. The method according to claim 1, wherein the steroidal anti-inflammatory agent is fluocinolone acetonide.

42. The method according to claim 15, wherein the steroidal anti-inflammatory agent is fluocinolone acetonide.

* * * * *